United States Patent
Ramella-Roman et al.

(10) Patent No.: US 10,349,837 B2
(45) Date of Patent: Jul. 16, 2019

(54) MATERIALS AND METHODS FOR NON-INVASIVELY MEASURING TEMPERATURE DISTRIBUTION IN THE EYE

(71) Applicants: Jessica Ramella-Roman, Miami, FL (US); Herbert Wertheim, Miami, FL (US); Pedro Lopez, Miami, FL (US); Yuqiang Bai, Miami, FL (US)

(72) Inventors: Jessica Ramella-Roman, Miami, FL (US); Herbert Wertheim, Miami, FL (US); Pedro Lopez, Miami, FL (US); Yuqiang Bai, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/863,389

(22) Filed: Jan. 5, 2018

(65) Prior Publication Data
US 2018/0192886 A1    Jul. 12, 2018

Related U.S. Application Data

(60) Provisional application No. 62/443,750, filed on Jan. 8, 2017.

(51) Int. Cl.
| | | |
|---|---|---|
| *A61B 5/01* | (2006.01) | |
| *G01K 13/00* | (2006.01) | |
| *G01N 21/47* | (2006.01) | |
| *A61B 3/14* | (2006.01) | |
| *A61B 3/00* | (2006.01) | |
| *A61B 5/00* | (2006.01) | |
| *G01K 11/00* | (2006.01) | |
| *A61B 3/10* | (2006.01) | |

(52) U.S. Cl.
CPC .............. *A61B 5/01* (2013.01); *A61B 3/0025* (2013.01); *A61B 3/10* (2013.01); *A61B 3/14* (2013.01); *G01K 11/00* (2013.01); *G01K 13/00* (2013.01); *G01K 13/002* (2013.01); *G01N 21/4788* (2013.01); *A61B 5/0062* (2013.01); *G01K 2213/00* (2013.01); *G01N 2021/479* (2013.01)

(58) Field of Classification Search
CPC ....... A61B 5/01; A61B 3/0025; A61B 5/0062; A61B 3/14; G01K 13/00; G01N 21/4788; G01N 2021/479
See application file for complete search history.

(56) References Cited

PUBLICATIONS

Aizu, Y., Asakura, T., "Coherent optical techniques for diagnostics of retinal blood flow." Journal of Biomedical Optics, Jan. 1999, 4(1): Abstract.
Fercher, A.F., Briers, J.D., "Flow visualization by means of single-exposure speckle photography." Optics Communications, Jun. 1981, 37(5): Abstract.
McCally, R.L., et al., "Laser Eye Safety Research at APL." John Hopkins APL Technical Digest, 2005, 26(1): 46-55.

*Primary Examiner* — Jack Dinh
(74) *Attorney, Agent, or Firm* — Saliwanchik, Lloyd & Eisenschenk (57) ABSTRACT

The present invention provides devices and methods for measuring the temperature distribution of an eye using non-invasive techniques. Embodiments of the present invention utilize laser speckle cross-correlation to determine the thermal distribution of an eye.

20 Claims, 10 Drawing Sheets

MATERIALS AND METHODS FOR NON-INVASIVELY MEASURING TEMPERATURE DISTRIBUTION IN THE EYE

BACKGROUND OF INVENTION

Sources such as the sun or lasers used in clinical settings can induce changes in temperature in the eye. The retina can suffer irreversible damages if exposed to heat out of physiological range (>37° C.). Current retinal temperature measurement modalities for animals are limited to invasive techniques. However, such invasive techniques cannot be generally utilized to measure the temperature distribution of the eye.

BRIEF SUMMARY

The present invention provides devices and methods for measuring the temperature distribution of an eye, particularly, the retina, using non-invasive techniques. The devices and methods can be used, for example, to assess the pathophysiological rate of ambient light-induced retinal temperature elevation.

In specific embodiments, the present invention utilizes laser speckle cross-correlation techniques.

DETAILED DISCLOSURE

The present invention provides devices and methods for measuring the temperature distribution of an eye of a subject using non-invasive techniques. In one embodiment the method of the invention measures the temperature distribution of the retina. The determination of the temperature distribution can be used in the diagnosis, and/or monitoring the progression of, an ocular pathology. In certain embodiments a confirmatory diagnostic procedure can also be performed. Optionally, treatment for the ocular disorder can be administered.

In preferred embodiments, the subject is a mammal, such as, for example, a human, a dog, a cat, cattle, or a horse.

Conditions that currently have no treatment such as non-exudative age-related macular degeneration (geographic atrophy) can be caused by changes in eye temperature. In accordance with the current invention, diagnostic prediction of age related macular degeneration can be readily provided accurately and quickly by, for example, an ophthalmologist.

The basic method for determining retinal temperature according to the present invention is to observe speckle contrast created by a coherent light source. Under proper conditions, a rough surface (a surface with RMS surface height variation that is large with respect to the laser light wavelength) being illuminated by a coherent light source will produce a speckle pattern. Any change in the material properties of the surface, including a change in temperature, will decrease speckle cross-correlation. This approach can be used to measure the temperature at specific locations (X, Y) throughout the retina.

More specifically, a first speckle pattern originating from a portion of the retina can be obtained by projecting a first beam onto the portion of the retina. A speckle size of at least 5×5 pixels is preferred. The speckle pattern is dependent on local optical properties and temperature and can have a wavelength of about 700 nm, in a range from 600 nm to 800 nm, or more specifically in a range from 650 nm to 750 nm (with a power that is preferably at or below 1 mWatt). The speckle pattern can then be altered by applying a short pulse of a second laser onto the portion of the retina while the first beam is continuously illuminating the portion of the retina. The second beam can have a wavelength of about 633 nm, or a range from 575 nm to 675 nm, or more specifically a range from 600 nm to 650 nm (with a power that is preferably at or below 1 mWatt). A second speckle pattern originating from the portion of the retina resulting from the first beam after the pulse of the second beam is then obtained. Speckle cross-correlation between the first speckle pattern and the second speckle pattern is then measured, and the temperature decay after the pulse second laser can be used to measure the temperature of the portion of the retina.

In some embodiments, the first and the second beams are scanned through different locations in the retina to measure temperatures in multiple locations in the retina. For example, beams can be scanned throughout the entire retina to determine the temperatures throughout the entire retina.

Another embodiment of the present invention includes applying two or more laser pulses onto the retina as the second beams. The first beam and the second beam can have different energy levels. For example, the first beam can have twice the energy of the second beam, and then the ground temperature of the retina can be measured. The laser can be aligned co-axially with the speckle illumination. According to the techniques disclosed herein, a speckle fundus imager can be fabricated to obtain real time imagery of the retina including temperature data.

Embodiments of the present invention can incorporate the use of laser speckle cross-correlation technology. Speckle based techniques can be used to measure very subtle changes in the index of refraction within a medium.

Data acquisition can be done by, for example, illuminating a retina with a coherent light (or electromagnetic radiation) source and imaging the retina with a CCD camera. This exploits the relationship between camera integration time and speckle lifetime. If the speckle lifetime is short compared to integration time, the contrast will be diminished. Furthermore, calculation of localized speckle contrast allows for the determination of speckle lifetime and velocity, which is inversely related to speckle lifetime.

A speckle-based imaging system according to the present invention can include a camera, an imaging system, and computer software and hardware that analyze the data captured by the imaging system.

Accordingly, certain embodiments of the invention provide a method for measuring a temperature of an area, comprising:
 a) illuminating the area with a first light beam,
 b) receiving a first speckle pattern produced by the first light beam from the area,
 c) illuminating the area with a second light beam,
 d) receiving a second speckle pattern produced by the first light beam from the area after illuminating the area with the second light beam in step c),
 e) calculating pixel cross-correlation between the first speckle pattern and the second speckle pattern, and
 f) measuring the temperature of the area based on the pixel cross-correlation determined in step e).

In some embodiments, the area is continuously illuminated with the first light beam throughout steps a) to d). In such embodiments, during step c), the area is illuminated with both the first beam and the second beam and in step d), the area is only illuminated with the first beam. In specific embodiments, step d) of receiving the second speckle pattern is performed between about 0.5 milliseconds (msec) to about 5 msec after step b), preferably, after about 0.75 msec to about 3 msec after step b), more preferably, between about 1 msec to 2 msec after step b), and even more preferably, about 1 msec after step b). As such, step c) can be performed for about 0.5 milliseconds (msec) to about 5 msec, preferably, for between about 0.75 msec to about 3 msec, more preferably, for between about 1 msec to 2 msec, and even more preferably, for about 1 msec.

In certain embodiments, the methods of the invention are used to determine the temperature of a surface in an eye of a subject, particularly, a human eye. Therefore, certain embodiments of the invention provide a method for measuring a temperature of an area in an eye, comprising the steps a) to f) described above.

The first light beam and the second light beam can have different energies. Preferably, the first light beam has twice the energy compared to the second light beam. Even more preferably, each of the first light beam and the second light beam has the energy of less than 1 mWatt.

The first light beam and the second light beam can also have different wavelengths. For example, the first light beam can have a wavelength between 600 nm to 800 nm, particularly, 650 nm to 750 nm, and more particularly, about 700 nm. The second light beam can have a wavelength between 600 nm to 650 nm, particularly, about 625 nm, and more particularly, about 633 nm.

The first and/or the second light beam can have a diameter of 0.5 mm and the first and/or the second light beam lasts for 1 about millisecond.

In some embodiments, the first light beam has a large diameter encompassing the whole retina. The speckle pattern includes many speckles with each speckle at least 3×3 pixels, preferably, 5×5 pixels.

In some embodiments, the first and second speckle patterns have 3×3 to 7×7 pixels, preferably, 4×4 to 8×8 pixels, more preferably, 5×5 to 7×7 pixels, and even more preferably, 5×5 pixels or 6×6 pixels.

The method of determining a temperature of a surface within an eye according to the invention can be extrapolated to determine the temperature distribution in an eye, particularly, in a human eye. As such, the invention provides a method for determining a temperature distribution in an eye, comprising:
 a) determining temperatures for a plurality of areas in the eye according to the method for measuring a temperature of an area in an eye, comprising:
   i) illuminating the area with a first light beam,
   ii) receiving a first speckle pattern produced by the light beam from the area,
   iii) illuminating the area with a second light beam,
   iv) receiving a second speckle pattern produced by the light beam from the area,
   v) calculating pixel cross-correlation between the first speckle pattern and the second speckle pattern, and
   vi) measuring the temperature of the area in the eye based on the pixel cross-correlation determined in step v); and
 b) determining the temperature distribution in the eye based on the temperatures of the plurality of areas in the eye.

In some embodiments, the area is continuously illuminated with the first light beam throughout sub-steps i) to iv) of step a). In such embodiments, during sub-step iii), the area is illuminated with both the first beam and the second beam and in sub-step iv), the area is only illuminated with the first beam. In specific embodiments, step iv) of receiving the second speckle pattern is performed between about 0.5 msec to about 5 msec after step ii), preferably, after about 0.75 msec to about 3 msec after step ii), more preferably, between about 1 msec to 2 msec after step ii), and even more preferably, about 1 msec after step ii). As such, step iii) can be performed for about 0.5 milliseconds (msec) to about 5 msec, preferably, for between about 0.75 msec to about 3 msec, more preferably, for between about 1 msec to 2 msec, and even more preferably, for about 1 msec.

Further embodiments of the invention provide an apparatus for performing the methods of the invention. In certain such embodiments, the invention provides a laser speckle imaging system, comprising a coherent light source, a camera, and a polarized single mode fiber.

The coherent light source can be a laser diode. The laser diode can emit a light having a wavelength between 600 to 800 nm, particularly, about 625 nm, 650 nm, 675 nm, 700 nm, 725 nm, 750 nm, 775 nm, or 800 nm.

The camera can comprise a polarizer and a lens, particularly, a 50 mm fl, F#1.3 lens. Lenses can be incorporated into the imaging system to filter and magnify light coming from the eye or retina. For optimal results, a resolution of up to, or greater than, 5, 6, 7, 8, or 9 μm/pixel is preferred.

In some embodiments, the laser speckle imaging system comprises a first laser that provides a first laser beam to an area to be illuminated, a second laser that provides the pulse second laser beam, a Galvanometer mirror, which optionally in conjunction with a dichroic, deflects the pulse second laser beam to the area. In certain embodiments, the area to be illuminated is on a plate.

In some embodiments, the area to be illuminated is a subject's retina. In such embodiments, the laser speckle imaging system is designed so that a subject can be positioned in a manner that the first and the second laser beams can be projected onto the subject's retina.

The laser speckle imaging system can further comprise a processing apparatus. Typically, a processing apparatus comprises a microprocessor, storage, bus system, and at least one user interface element, optionally with user input. The user interface element can be chosen from a display, a keyboard, and a mouse. In some embodiments, the system comprises at least one integrated circuit and/or at least one semiconductor.

The processing apparatus receives from the camera the data corresponding to: a first light speckle pattern produced by a first illumination of a surface by a first light beam emitted by the coherent light source and a second light speckle pattern produced by a second illumination of the surface by a second light beam emitted by the coherent light source. The processing apparatus then compares the first light speckle pattern with the second light speckle pattern and provides the temperature of the surface. Acquisition and analysis software can be custom fabricated using a variety of commercially available tools (e.g., Matlab, Natick, Mass.).

In certain embodiments, in the laser speckle imaging system of the coherent light source is configured to illuminate a surface of an eye. In certain other embodiments, in the laser speckle imaging system, the camera is configured to receive light speckle pattern from the surface of the eye. Such laser speckle imaging system can be used to determine temperature of an area within an eye of a subject, particularly, a human eye.

The laser speckle imaging system of the invention configured to illuminate and image a surface of an eye can be used to determining a temperature of an area in an eye. Such method comprises:

a) illuminating the area with a first light beam,
b) receiving a first speckle pattern produced by the first light beam from the area,
c) illuminating the area with a second light beam,
d) receiving a second speckle pattern produced by the first light beam from the area after illuminating the area with the second light beam in step c),
e) calculating pixel cross-correlation between the first speckle pattern and the second speckle pattern, and
f) measuring the temperature of the area based on the pixel cross-correlation determined in step e).

In some embodiments, the area is continuously illuminated with the first light beam throughout steps a) to d). In such embodiments, during step c), the area is illuminated with both the first beam and the second beam and in step d), the area is only illuminated with the first beam. In specific embodiments, step d) of receiving the second speckle pattern is performed between about 0.5 msec to about 5 msec after step b), preferably, after about 0.75 msec to about 3 msec after step b), more preferably, between about 1 msec to 2 msec after step b), and even more preferably, about 1 msec after step b). As such, step c) can be performed for about 0.5 milliseconds (msec) to about 5 msec, preferably, for between about 0.75 msec to about 3 msec, more preferably, for between about 1 msec to 2 msec, and even more preferably, for about 1 msec.

The first light beam and the second light beam have different energies. Preferably, the first light beam has twice the energy compared to the second light beam. Even more preferably, each of the first light beam and the second light beam has the energy of less than 1 mWatt, for example, below 0.9, 0.8, 0.7, 0.6, or 0.5 mWatt.

The first light beam and the second light beam can also have different wavelengths. For example, the first light beam can have a wavelength between 600 nm to 800 nm, particularly, 650 nm to 750 nm, and more particularly, about 700 nm. The second light beam can have a wavelength between 600 nm to 650 nm, particularly, about 625 nm, and more particularly, about 633 nm.

The first and/or the second light beam can have a diameter of 0.5 mm and the first and/or the second light beam lasts for 1 about millisecond.

The first and second speckle patterns have 3×3 to 7×7 pixels, preferably, 4×4 to 8×8 pixels, more preferably, 5×5 to 7×7 pixels, and even more preferably, 5×5 pixels or 6×6 pixels.

Figure 1A:
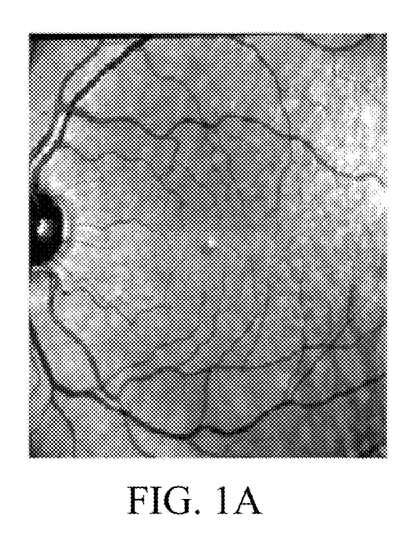
FIG. 1A is an original retina fundus image showing the vasculature of a healthy volunteer.
Figure 1B:
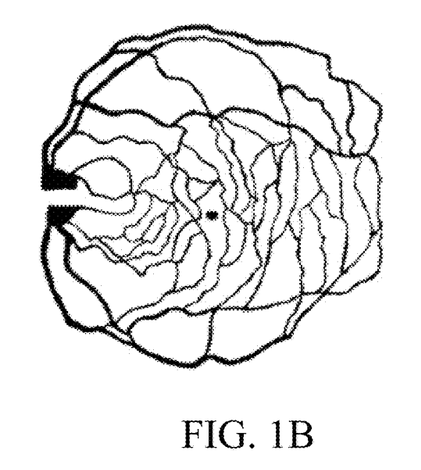
FIG. 1B is a filtered version of the retina image of FIG. 1A showing the vasculature of a healthy volunteer.
Figure 1C:
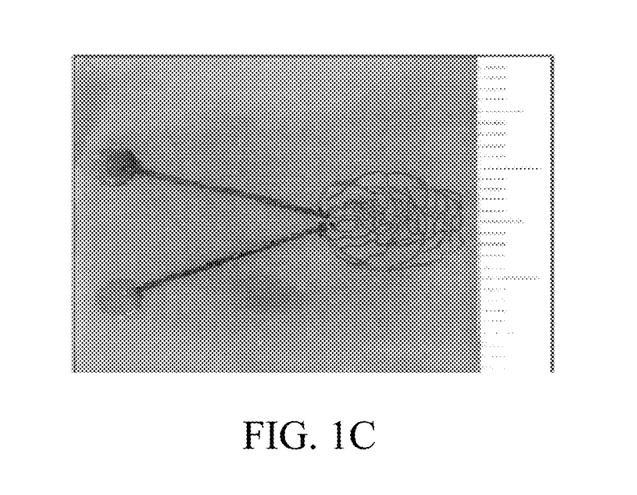
FIG. 1C is a realized phantom of FIG. 1A on an absorbing and scattering epoxy layer (divisions on the right hand side are in mm).
Figure 2:
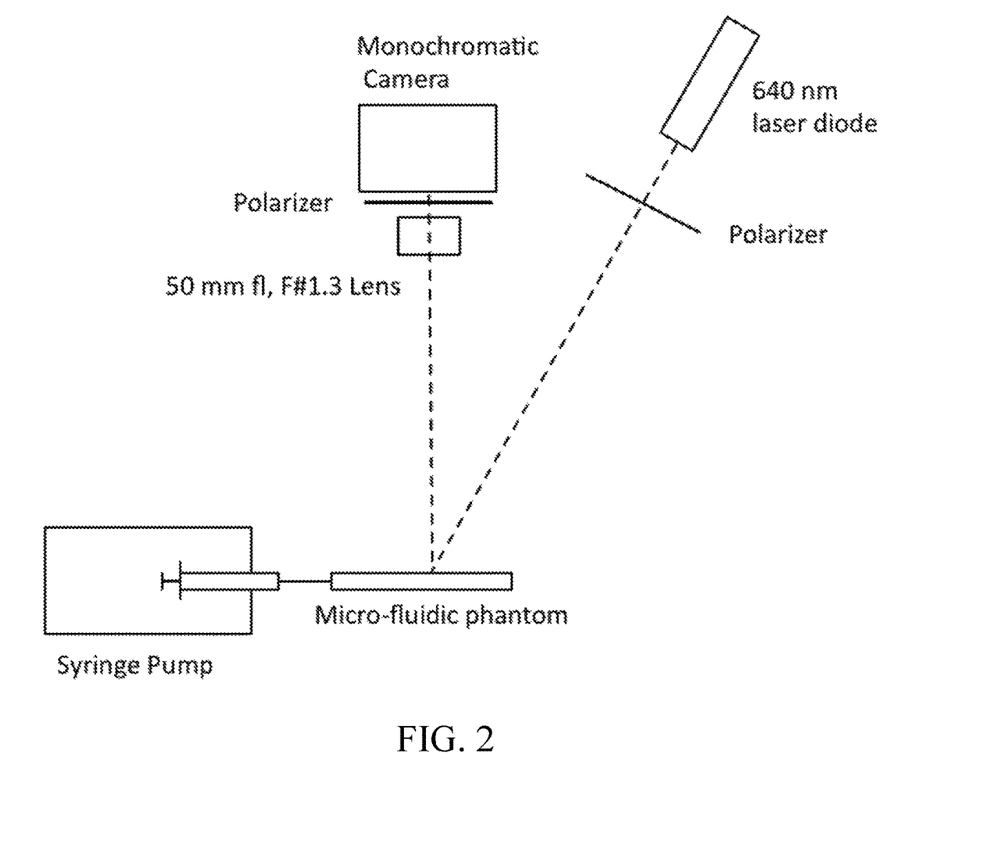
FIG. 2 is an image of a speckle imaging system according to an embodiment of the present invention.
Figure 5:
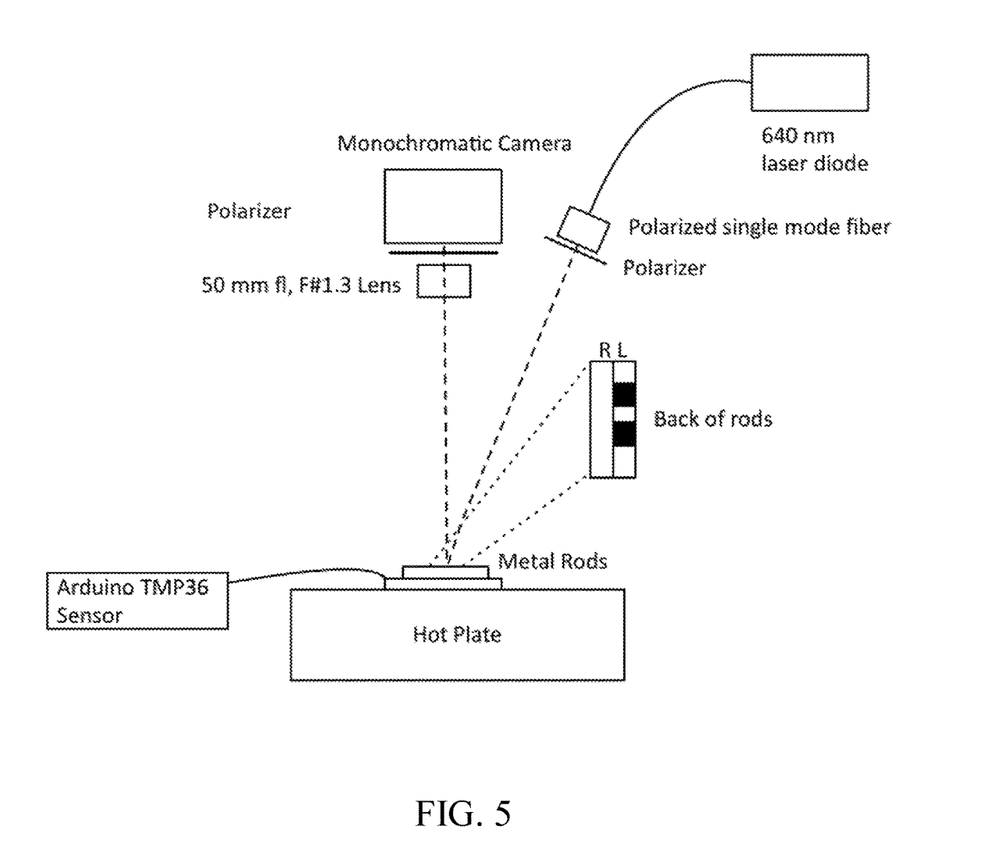
FIG. 5 provides an embodiment of the laser speckle imaging system. As the temperature of the hot plate increases, the LSI system's coherent light source illuminates the metallic rod's surface. The light source produces a speckle pattern on the rod and a stack of images of the speckle pattern are acquired using software (Matlab, Natick, Mass.). Any change of the material property, due to heat, will decrease the speckle autocorrelation.

An example of using the laser speckle imaging system to capture retinal images is described in FIGS. 2 and 5. Examples of retinal phantoms captured using an embodiment of the present invention is represented in FIG. 1.

Definitions

As used herein, the singular forms "a", "an" and "the" are intended to include the plural forms as well, unless the context clearly indicates otherwise. Further, to the extent that the terms "including", "includes", "having", "has", "with", or variants thereof are used in either the detailed description and/or the claims, such terms are intended to be inclusive in a manner similar to the term "comprising."

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e., the limitations of the measurement system. Where particular values are described in the application and claims, unless otherwise stated the term "about" meaning within an acceptable error range for the particular value should be assumed. In the context of compositions containing amounts of ingredients where the term "about" is used, these compositions contain the stated amount of the ingredient with a variation (error range) of 0-10% around the value (X±10%).

In the present disclosure, ranges are stated in shorthand, to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, and 0.7-1.0.

When ranges are used herein, combinations and subcombinations of ranges (e.g., subranges within the disclosed range), specific embodiments therein are intended to be explicitly included.

As used herein the phrase "pixel cross-correlation" between a first speckle pattern and a second speckle pattern represents the difference in speckle patterns. Such differences include differences in the pixel locations, pixel intensity, pixel number, etc.

A greater understanding of the present invention and of its many advantages may be had from the following examples, given by way of illustration. The following examples are illustrative of some of the methods, applications, embodiments and variants of the present invention. It is, of course, not to be considered as limiting the invention. Numerous changes and modifications can be made with respect to the invention.

Example 1

A laser speckle imaging system was constructed to measure the temperature of retinal phantoms, as shown in FIG. 1. The system can be seen in the image of FIG. 2. The system included a 12-bit, monochrome camera (Pantera® TF 1M60, Dalsa, Ontario, Canada) with 1024×1024 resolution, and maximum frame rate of 60 Hz. A 50 mm focal length F#1.3 lens (Precise Optics, Bay Shore N.Y.) was used with the camera for magnification and to obtain resolutions of up to 7 μm/pixel. The light source was a 640 nm, 200 mW diode laser (Melles Griot, Longmont, Colo.), connected to a single mode fiber.

Acquisition was conducted automatically with custom software (Matlab, Natick, Mass.). The laser acted as a coherent light source and the camera was used to observe speckle contrast. Based on the speckle contrast measurements, the temperature at specific locations (X, Y) throughout the retina was determined. A speckle size of at least 5×5 pixels was utilized. The speckle pattern was then altered by applying a short pulse of laser light onto the retina. The pulse of laser light had a diameter of 0.50 mm, a wavelength of 633 nm, and it lasted for 1 msec. The power applied by the laser was maintained well below levels that would cause retinal damage.

Figure 3:
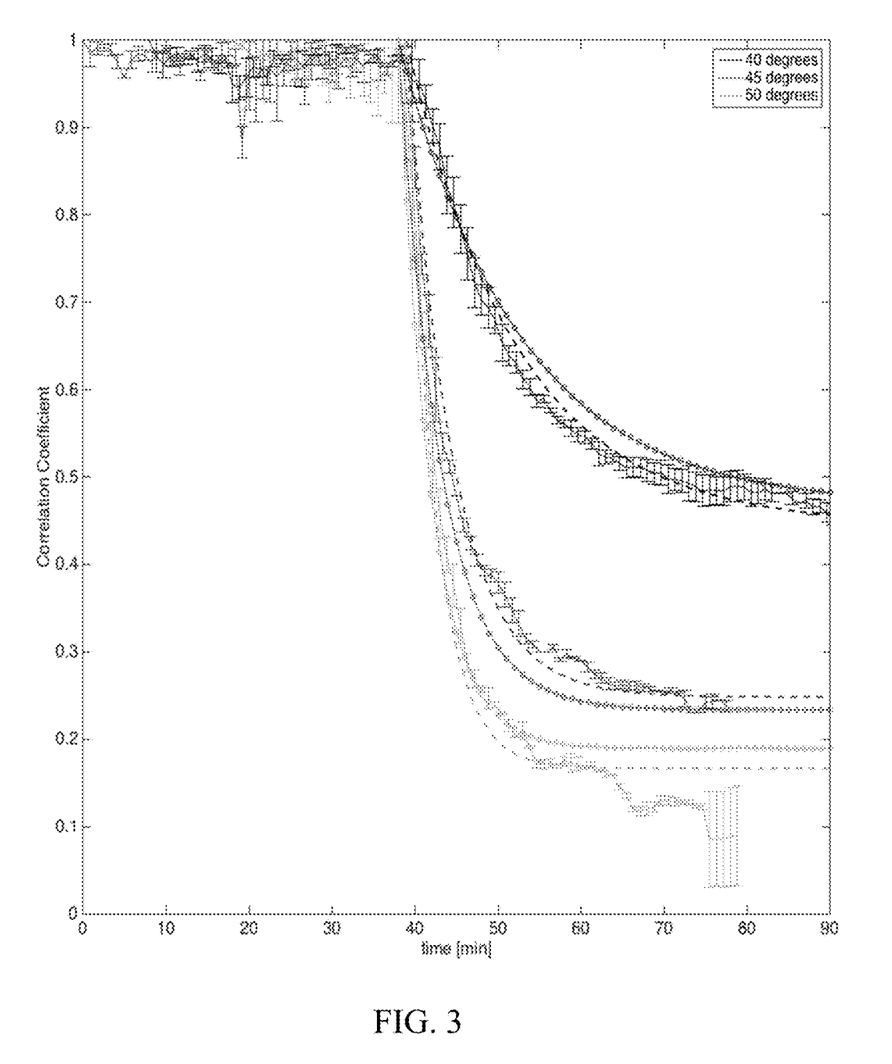
FIG. 3 is a graph of correlation coefficients versus time, showing speckle cross-correlation with a temperature dependent model.
Figure 4:
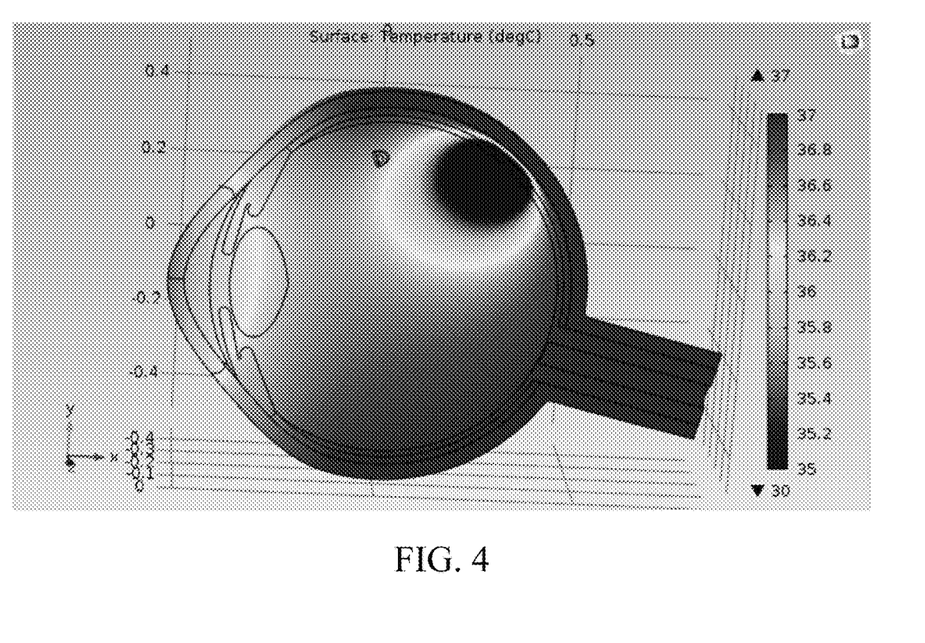
FIG. 4 shows modeling heat distribution in the eye. Heat spots in eye can influence the temperature in other areas. A localized change in retinal temperature induced an asymmetric temperature distribution in the eye. External temperature measurement (FLIR) cannot be used to determine retinal temperature differences.

Speckle cross-correlation was then measured, and the temperature decay after the pulse was used to measure the ground state temperature. Experimental results of this procedure can be seen in FIG. 3. In the graph of FIG. 3, the speckle cross-correlation was measured for identical samples (eye mimicking phantoms) that were brought to three different temperatures (40, 45 and 50 degrees respectively). The graph of FIG. 3 shows both the means and standard deviations for each of the experiments. Autocorrelation techniques were used to form a temperature dependent model using the experimental data, as seen by the solid lines.

Further analysis was conducted using two laser pulses having controlled energy. The laser pulses were applied to the retinas. The first pulse had twice the energy of the second. The ground temperature of the retina was then measured, which in one test was 23° C.

Example 2

Inverse thermal models, depicting the thermal distribution of the eye, suggest that local retinal temperature cannot be extrapolated using standard corneal surface temperature measurements. An LSI system to measure the micro changes in index of refraction resulting from an increase of local temperature are provided. Speckle cross-correlation models are used to highlight changes in speckle patterns as the temperature changes.

In certain embodiments, the LSI system comprises a monochrome camera, for example, a 12-bit monochrome camera, a lens, for example, a 50 mm focal length F#1.3 lens, a diode laser, for example, a diode laser centered at 640 nm, and a polarized single mode fiber and preliminary studies relating temperature to speckle cross correlation. The LSI system can be designed to provide a non-contact imaging system for clinical use in humans, for example, measuring temperature measurements of human eye, particularly, human retina.

In the LSI system described in FIG. 5, as the temperature of the hot plate increases, the LSI system's coherent light source illuminates the metallic rod's surface. The light source produces a speckle pattern on the rod and a stack of images of the speckle pattern are acquired using software (Matlab, Natick, Mass.). Any change of the material property, due to heat, will decrease the speckle autocorrelation.

Figure 6:
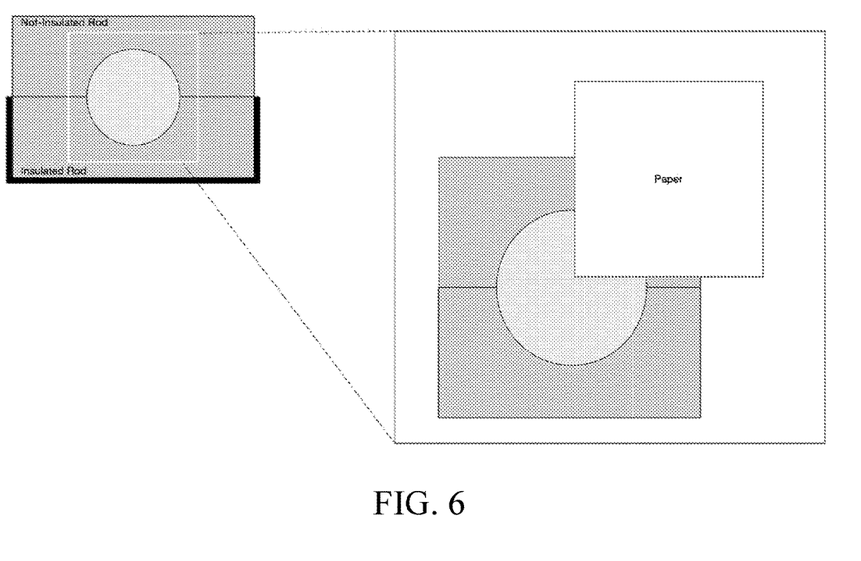
FIG. 6 provides a close-up view of sample with laser beam. White arrow and paper corner denote start of vertical separation between insulated and non-insulated parts of rod.
Figure 7:
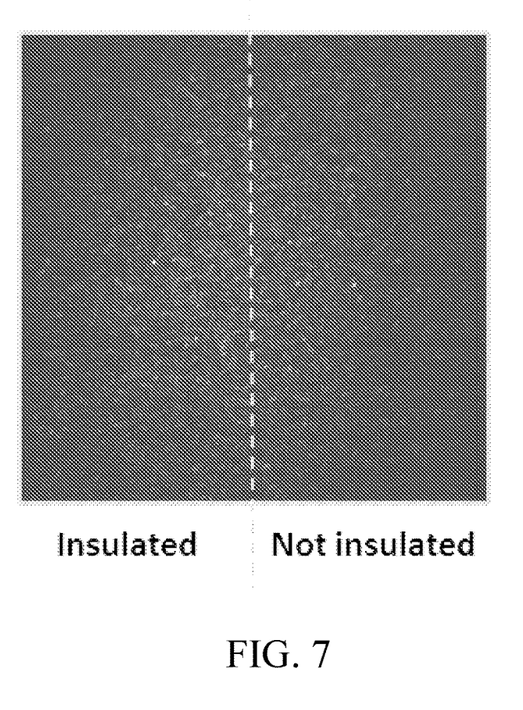
FIG. 7 shows insulated and not insulated areas of the metal rod. Isolation (electrical tape) is placed beneath rod before imaging.

The difference in cross-correlation based on the temperature is demonstrated based on the difference between the two portions of an identical surface having different temperatures. As shown in FIG. 6, one area of a metal rod is heated and another area of the metal rod is insulated using an electrical tape.

Figure 8:
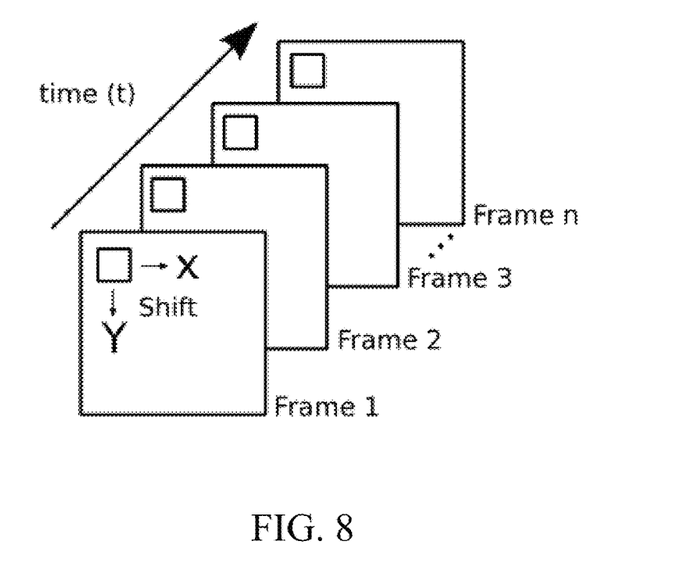
FIG. 8 shows pixel cross-correlation. Pixel cross-correlation was calculated on each frame of the image stack over time.
Figure 9:
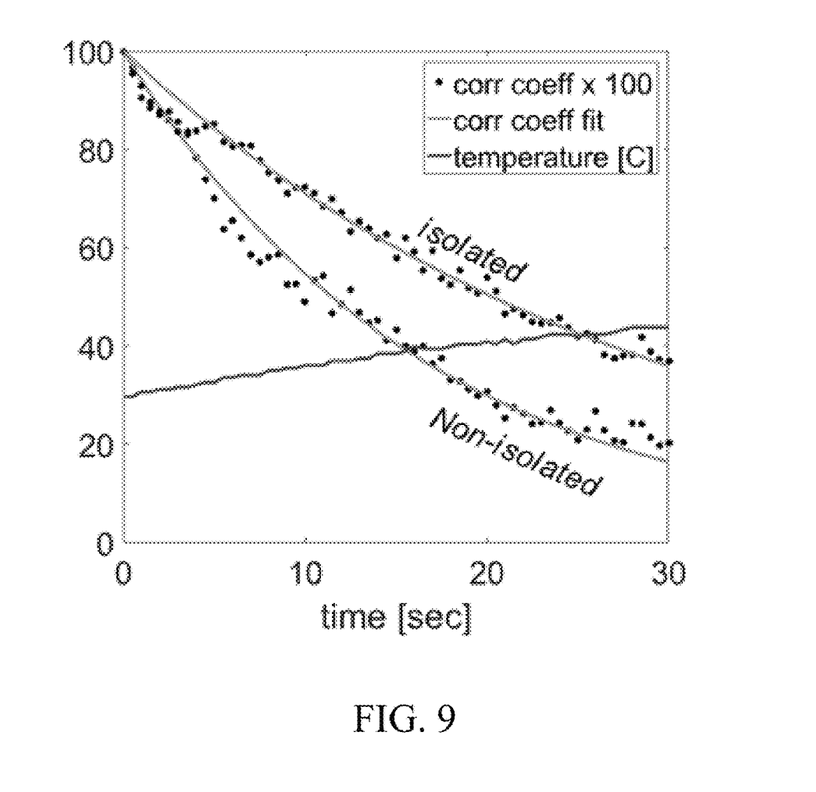
FIG. 9 shows effects of temperature on cross-correlation plots. As the temperature increases from 30° C. to 42° C., an exponential decay occurs in both cross-correlation plots. The non-insulated rod shows faster decorrelation than the insulated rod.
Figure 10A:
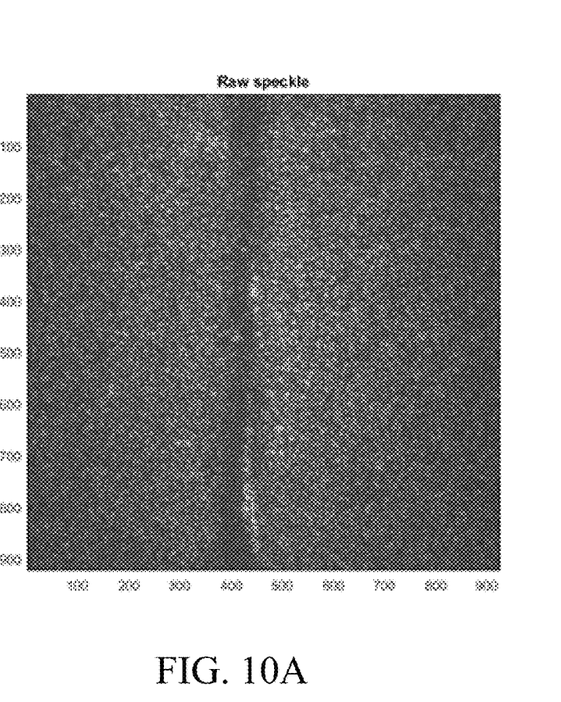
FIG. 10A shows raw speckle image showing insulated [left] and non-insulated [right].
Figure 10B:
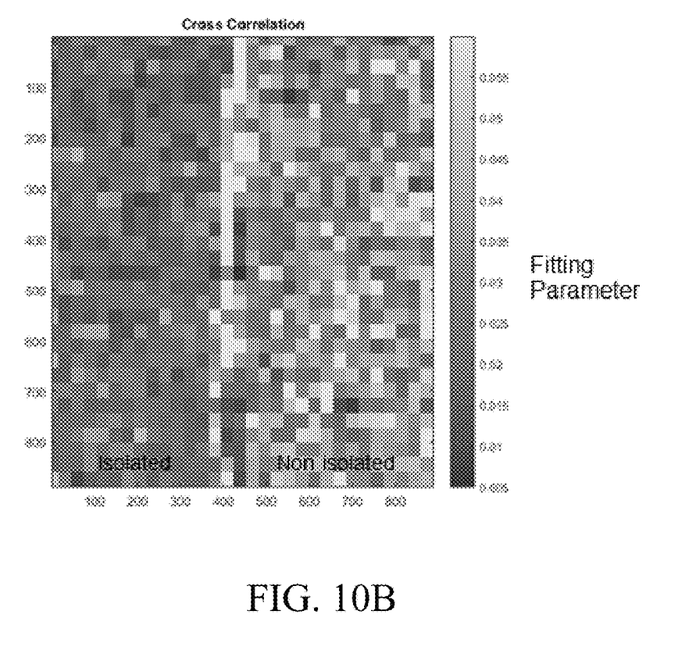
FIG. 10B shows cross correlation of image stack showcasing the difference in fitting parameter between both sides. The non-insulated side shows faster decorrelation.
Figure 11:
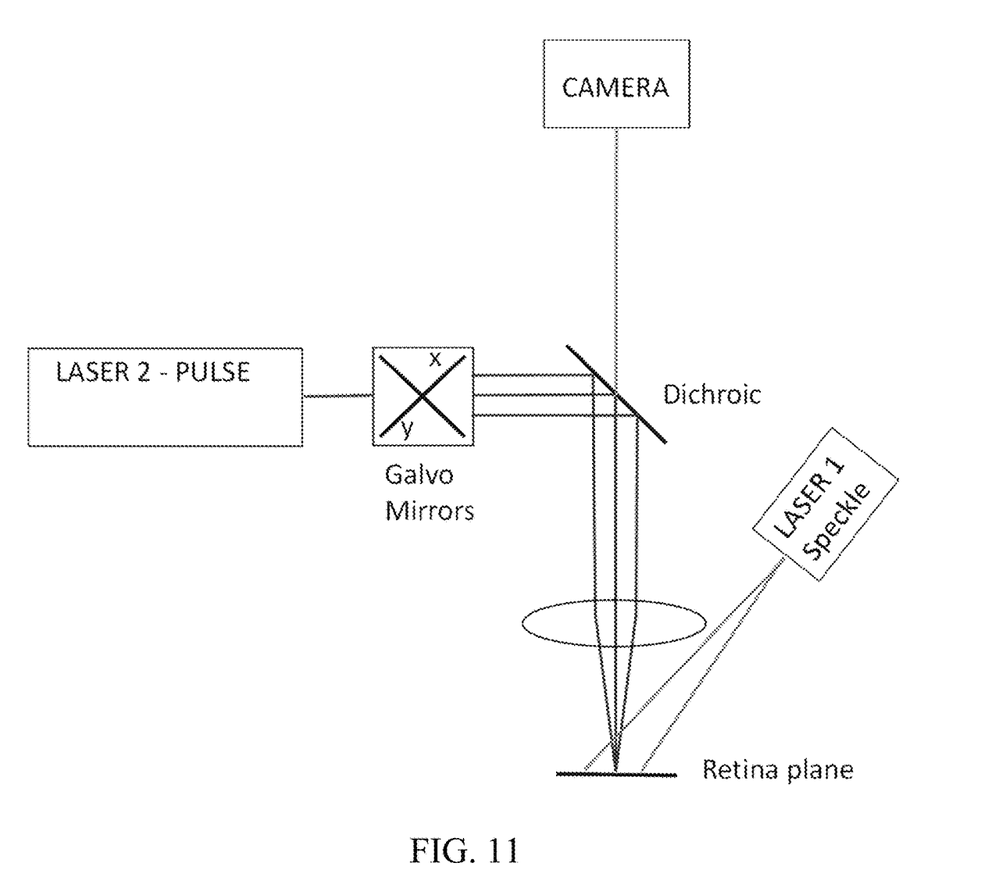
FIG. 11 shows schematic representation of an exemplary laser speckle imaging system of the invention that could be used to determine temperature of a portion of the retina or of the entire retina.

Pixel cross-correlation was calculated over time on each frame of the image stack arising from the insulated and non-insulated areas of the metal rod (FIG. 8). As the temperature increases, exponential decay develops in cross-correlation plots from both the insulated and non-insulated metal rods. However, the non-insulated rod shows faster decorrelation than the insulated metal rod (FIG. 9).

The faster decorrelation in the non-insulated metal rod versus the insulated metal rod is shown in FIGS. 8A and 8B. FIG. 8A shows raw speckle image of insulated and non-insulated metal rod areas. FIG. 8B shows speckle image decorrelation in the insulated and non-insulated metal rod areas. The non-insulated metal rod area exhibits higher speckle image decorrelation. As such, FIGS. 8A and 8B demonstrate that speckle images from a surface having higher temperature shows faster decorrelation compared to speckle images from a surface having lower temperature. Therefore, the rate of decorrelation in speckle images from a surface can be used to determine the temperature of the surface.

We claim:

1. A method for measuring a temperature of an area in an eye, comprising:
    a) illuminating the area with a first light beam,
    b) receiving a first speckle pattern produced by the first light beam from the area,
    c) illuminating the area with a second light beam,
    d) receiving a second speckle pattern produced by the first light beam from the area after illuminating the area with the second light beam in step c),
    e) calculating pixel cross-correlation between the first speckle pattern and the second speckle pattern, and
    f) measuring the temperature of the area based on the pixel cross-correlation determined in step e).

2. The method of claim 1, wherein the area in the eye is continuously illuminated with the first light beam throughout steps a) to d).

3. The method, according to claim 1, wherein the eye is a human eye.

4. The method, according to claim 1, wherein the area in the eye is in the retina.

5. The method, according to claim 1, wherein the first light beam and the second light beam have different energies.

6. The method, according to claim 5, wherein the first light beam has twice the energy compared to the second light beam.

7. The method, according to claim 6, wherein each of the first light beam and the second light beam has the energy of less than 1 mWatt.

8. The method, according to claim 1, wherein the first light beam has a wavelength between 650 nm to 750 nm and the second light beam has a wavelength between 600 nm to 650 nm.

9. The method of claim 1, wherein the first and second speckle patterns have at least 5×5 pixels.

10. The method of claim 9, wherein second light beam has a diameter of 0.5 mm and the second light beam lasts for 1 millisecond.

11. A method for determining a temperature distribution in an eye, comprising:
   a) determining temperatures for a plurality of areas in the eye according to the method of claim 1,
   b) determining the temperature distribution in the eye based on the temperatures of the plurality of areas in the eye.

12. A laser speckle imaging system, comprising a first laser that provides a first laser beam and is configured to illuminate an area, a second laser that provides a pulse second laser beam, a Galvanometer mirror, which optionally in conjunction with a dichroic, is configured to illuminate the area with the pulse second laser beam, and a camera configured to receive speckle patterns from the area.

13. The laser speckle imaging system of claim 12, wherein each of the first laser and the second laser is a laser diode and the camera comprises a polarizer and a 50 mm fl, F#1.3 lens.

14. The laser speckle imaging system of claim 12, wherein the first laser is configured to emit the first beam of a wavelength between 650 nm to 750 nm and the second laser is configured to emit the second beam of a wavelength between 600 nm to 650 nm.

15. The laser speckle imaging system of claim 14, further comprising a processing apparatus, wherein the processing apparatus receives from the camera the data corresponding to: a first light speckle pattern produced by a first illumination of a surface by a first light beam emitted by the first laser and a second light speckle pattern produced by a second illumination of the surface by a second light beam emitted by the first laser, wherein between the first and the second illuminations of the surface by the first laser the surface is illuminated by a pulse second beam emitted by the second laser, and wherein the processing apparatus compares the first light speckle pattern with the second light speckle pattern and provides the temperature of the surface.

16. The laser speckle imaging system of claim 15, wherein the illuminated surface is in a subject's retina and the laser speckle imaging system is configured to position the subject in a manner that the first and the second laser beams are projected onto the subject's retina.

17. A method for measuring a temperature of an area, comprising:
   a) illuminating the area with a first light beam,
   b) receiving a first speckle pattern produced by the first light beam from the area,
   c) illuminating the area with a second light beam,
   d) receiving a second speckle pattern produced by the first light beam from the area after illuminating the area with the second light beam in step c),
   e) calculating pixel cross-correlation between the first speckle pattern and the second speckle pattern, and
   f) measuring the temperature of the area based on the pixel cross-correlation determined in step e).

18. The method, according to claim 17, wherein the first light beam and the second light beam have different energies.

19. The method, according to claim 17, wherein the first light beam has twice the energy compared to the second light beam.

20. The method, according to claim 17, wherein the first light beam and the second light beam has energy of less than 1 mWatt.

* * * * *